United States Patent [19]

Sugiura et al.

[11] 4,333,512

[45] Jun. 8, 1982

[54] METHOD OF QUICKLY PREDICTING THE DEGREE OF NODULARITY OF SPHEROIDAL GRAPHITE CAST IRON FROM A MOLTEN IRON SAMPLE

[75] Inventors: Taku Sugiura, Nagoya; Katsuya Fukuoka, Chita; Tomihiko Inoue, Tsushima; Masayoshi Kanbe, Toyoake; Toshio Iwama, Nagoya, all of Japan

[73] Assignee: Yahagi Iron Co., Ltd., Nagoya, Japan

[21] Appl. No.: 39,432

[22] Filed: May 15, 1979

[30] Foreign Application Priority Data

May 17, 1978 [JP] Japan ............................. 53-58640

[51] Int. Cl.³ .............................................. B22D 2/00
[52] U.S. Cl. ............................. 164/453; 164/150; 164/155
[58] Field of Search ............................ 164/55–58, 164/4, 154, 150, 155

[56] References Cited

U.S. PATENT DOCUMENTS 3,670,558  6/1972  Ryntz et al. ........................ 73/17 R
3,991,808  11/1976 Nieman et al. ...................... 164/154

OTHER PUBLICATIONS

"Problem in Programming Control Computer" by M. E. Brooks, Automation, 2/1963.
"Prediction of Nodular Iron Microstructure Using Thermal Analysis" by Ryntz et al, AFS Transactions vol. 79, 1971, pp. 141–144.
"Thermal Analysis For Structure Control" by Loper, et al., International Symposium Metall. Cast Iron (Swiss), 1974, pp. 626-657.
"Study of Nucleation and Growth of Graphite in Mg--Treated Cast Iron by Means of Thermal Analysis" by Backerud, et al. International Symposium Metall. Cast Iron (Swiss), 1974, pp. 625-637.

Primary Examiner—R. L. Spruill
Assistant Examiner—K. Y. Lin
Attorney, Agent, or Firm—Young & Thompson

[57] ABSTRACT

A method of quickly predicting the degree of nodularity of spheroidal graphite cast iron from a molten iron sample is disclosed. The method comprises steps of reading out the lowest temperature $T_{EU}$ due to undercooling and the highest temperature $T_{EM}$ due to recalescence subsequent to the undercooling which occur at the time of eutectic solidification of a number of samples of molten iron for spheroidal graphite cast iron during cooling and solidifying under a predetermined cooling condition; reading out an elapsed time Z from the lowest temperature $T_{EU}$ to the highest temperature $T_{EM}$; determining constants a, b, c and e in the following formula which shows a relation between the values of the thus read out temperatures and the elapsed time and any of the characteristics $D_S$ showing the degree of nodularity of spheroidal graphite cast iron selected from the percentage of spheroidal graphite, the percentage of residual magnesium, the tensile strength of the elongation of the cast iron after solidification; and obtaining the characteristics $D_S$ of the iron for spheroidal graphite cast iron, of which the degree of nodularity is unknown, by substituting $T_{EU}$, $T_{EM}$ and Z read out during cooling and solidifying of a molten sample of said iron under the predetermined cooling condition into the above formula:

$$D_S = a + bt_{EM} + c\Delta T_E + eZ$$

where $\Delta T_E$ is a difference between $T_{EM}$ and $T_{EU}$.

5 Claims, 5 Drawing Figures

FIG. 1
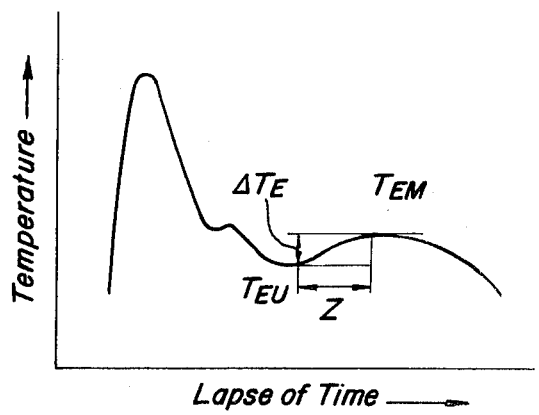
FIG. 2
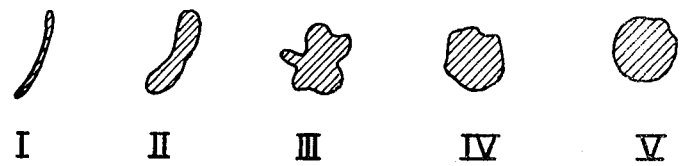
I  II  III  IV  V
FIG. 3
| Percentage of Spheroidal Graphite (%) / Pattern Display | 1-1 | 1-2 | 2-1 | 2-2 | 3-1 | 3-2 |
|---|---|---|---|---|---|---|
| 0~40 |  |  |  |  | ● | ● |
| 41~50 |  |  |  | ● | ● | ● |
| 51~60 |  |  | ● | ● | ● | ● |
| 61~70 |  | ● | ● | ● | ● |  |
| 71~80 |  | ● | ● | ● |  |  |
| 81~90 | ● | ● | ● |  |  |  |
| ≧ 91 | ● | ● |  |  |  |  |

METHOD OF QUICKLY PREDICTING THE DEGREE OF NODULARITY OF SPHEROIDAL GRAPHITE CAST IRON FROM A MOLTEN IRON SAMPLE

BACKGROUND OF THE INVENTION

The present invention relates to a method of quickly predicting the degree of nodularity of spheroidal graphite cast iron from a molten iron sample and an apparatus thereof, particularly relates to a method and an apparatus thereof, wherein the relation between temperature and time of a sample of molten iron for spheroidal graphite cast iron during cooling and solidification is measured by thermal analysis, three parameters strongly correlated to the degree of nodularity of spheroidal graphite cast iron are substituted into a formula previously statistically obtained from a series of experiments, and a result is obtained by operational process.

Spheroidal graphite cast iron has many excellent characteristics such as mechanical and physical properties, weldability, machinability and the like as compared with flaky graphite cast iron, but many problems as to manufacture remain unsettled.

That is, the degree of nodularity of molten iron for spheriodal graphite cast iron and further the quality of a product may be determined by the property of base iron, which is influenced by, for example, kind of melting raw material, chemical composition, history of melting treatment, melting process or the techniques of nodulizing treatment which is influenced by for example treated amount, treating temperature, treating procedure, kind and amount of added nodulant, etc. Thus, as compared with the flaky graphite cast iron, the spheroidal graphite cast iron has many manufacturing factors influencing upon the quality of a product, so that it is very difficult to positively control all these manufacturing factors.

In general, the degree of nodularity of spheroidal graphite cast iron is predicted directly by the percentage of spheroidal graphite based on observation of the structure of a sample cast under the same condition as castings or a sample piece attached to the casting itself through a microscope or determined indirectly from the mechanical properties such as tensile strength, elongation or the like, percentage of residual magnesium added as nodulant (residual Mg amount) and the like, which are significantly correlated to the degree of nodularity.

The determination based on the above measurement results is reliable but both the measurement and the determination take a long time, and even the observation of structure, which is deemed to be most quickly made, takes several hours after pouring, and when its degree of nodularity is predicted as bad, pouring would be ended and it is too late to take necessary action, a casting turns out inferior, and an economical loss is fatal in manufacture.

Casting industry has, therefore earnestly asked for the development of a method for quickly and precisely predicting the degree of nodularity of molten iron for spheroidal graphite cast iron (hereinafter referred to as SG molten iron), i.e., the nodularity after solidification of the molten iron before pouring the iron into molds immediately after nodulizing treatment to take necessary measures without delay.

As well known, the degree of nodularity of molten iron at the time of casting depends basically upon a residual Mg amount in molten iron or percentage of spheroidal graphite in the solidified state immediately after a nodulizing treatment. The decrease in a residual Mg amount or the lowering of the percentage of spheroidal graphite from the nodulizing treatment to the pouring depends upon the standard working conditions of each foundry shop, such as a maintaining temperature and time of the molten iron, a shape and a size of a ladle used and the like. Therefore, if the degree of nodularity of molten iron for spheroidal graphite cast iron immediately after a nodulizing treatment can be predicted, whether to be poured or not to be poured can be determined on the basis of the standard working conditions of each foundry shop and it becomes possible to avoid any reject manufactured by pouring an ill-treated molten iron.

In the process of cooling and solidifying the SG molten iron, a shape of a cooling curve obtained by thermal analysis (a curve showing the relation between the lapse of time and the temperature of a sample) closely relates to the degree of nodularity of spheroidal graphite cast iron after solidification, so that the so-called thermal analysis method is proposed recently; namely, an SG molten iron sample immediately after nodulizing treatment is tested by thermal analysis and the degree of nodularity of the SG molten iron is predicted from the differences of the process of temperature change before pouring into a mold. For example, a molten iron sample taken from the SG molten iron is poured into a sample mold (cup), a cooling curve is record-traced with the use of a suitable thermoelectric pyrometer and the degree of nodularity of the SG molten iron is predicted from the differences in shape of the curve obtained. This method is, however, to compare the curve with more than several tens of classification beforehand prepared with respect to the shapes of cooling curves and the degrees of nodularity of many examples, and to satisfy quickness of measurement, but comparison and analysis are complicated and troublesome, so that there is the possibility of being occupied by a subjective point of view and making a large error, and as a result, this method is not practically used at foundry shops.

As another method, a cooling curve being utilized in the same manner, a primary crystallization temperature, the lowest temperature by undercooling and the highest temperature due to recalescence subsequent to the undercooling, both of which occur at the time of eutectic solidification, are measured from the curve with the eye, and from a relation with the temperatures thus obtained by eye measurement the degree of nodularity of SG molten iron and carbide content are predicted. According to this method, quickness of measurement can be satisfied in the same manner as in the former method, but inaccurate readings of the lowest temperature and the highest temperature caused by a pyrometer which does not display numerical values result in an error, and, furthermore, resolving power of thermoelectromotive force of the pyrometer is insufficient and time parameters of temperature change, which are important for predicting the degree of nodularity of SG molten iron, are not taken into consideration, so that this method cannot obtain sufficient precision and is not practically used at the foundry shop.

Further, as a further method of utilizing a cooling curve, the degree of nodularity of SG molten iron is estimated from a single correlation with such as the lowest temperature by undercooling, the highest temperature due to recalescence, which occur at the time of eutectic solidification, a difference between both the temperatures, the maximum inclination angle of a curve from the lowest temperature to the highest temperature or the like. According to this method, as well as the two preceding methods, quickness can be satisfied, but there are an error for reading the lowest and highest temperatures, insufficient resolving power of thermoelectromotive force and deficient prediction standard with the use of a single correlation only, so that sufficient precision cannot be obtained, and as this method can only be applied to hypoeutectic SG molten iron, while almost all foundry shops manufacture spheroidal graphite cast iron from hyper-eutectic molten iron at present, this method is impossible to be used at the foundry shop.

At all events, as to prediction of the degree of nodularity of SG molten iron, if reliability has priority, it takes a long time for obtaining a result. In a conventional method with the aid of a thermal analysis method, quickness of measurement can be satisfied, but sufficient reliability cannot be obtained for the reason mentioned in the preceding. Further, the applicable composition of molten iron is limited, so that there is no method practically usable at the foundry shop.

SUMMARY OF THE INVENTION

An object of the present invention is to provide a method by removing the above-mentioned various disadvantages accompanied with the prior method and an apparatus directly used for carrying out the method.

According to the present invention a method of quickly predicting the degree of nodularity of spheroidal graphite cast iron from a molten iron sample comprises steps of reading out the lowest temperature $T_{EU}$ due to undercooling and the highest temperature $T_{EM}$ due to recalescence subsequent to the undercooling which occur at the time of eutectic solidification of a number of samples of molten iron for spheroidal graphite cast iron during cooling and solidifying under a predetermined cooling condition; reading out an elapsed time Z from the lowest temperature $T_{EU}$ to the highest temperature $T_{EM}$; determining constants a, b, c and e in the following formula which shows a relation between the values of the thus read out temperatures and the elapsed time and any of the characteristics $D_S$ showing the degree of nodularity of spheroidal graphite cast iron selected from the percentage of spheroidal graphite, the percentage of residual magnesium, the tensile strength or the elongation of the cast iron after solidification; and obtaining the characteristics $D_S$ of the iron for spheroidal graphite cast iron, of which the degree of nodularity is unknown, by substituting $T_{EU}$, $T_{EM}$ and Z read out during cooling and solidifying of a molten sample of said iron under the predetermined cooling condition into the above formula:

$$D_S = a + bT_{EM} + c\Delta T_E + eZ$$

where $\Delta T_E$ is a difference between $T_{EM}$ and $T_{EU}$.

According to the present invention an apparatus for quickly predicting the degree of nodularity of spheroidal graphite cast iron from a molten iron sample comprises a sampling mold provided with a hot junction for pouring a sample of molten iron for spheroidal graphite cast iron; an analog-digital converter for converting a temperature change as an analog signal measured at the hot junction into a digital amount; a means for successively storing numerical values of said digital amount read at intervals of a predetermined time, determining and storing those agreed to the predetermined condition among the numerical values as the lowest temperature $T_{EU}$ and the highest temperature $T_{EM}$ of eutectic solidification, and further storing a time Z between times showing said $T_{EU}$ and $T_{EM}$; and an operational processing means for substituting said $T_{EU}$, $T_{EM}$ and Z of molten iron of which the degree of nodularity is unknown into the following formula obtained from a number of samples of molten iron for spheroidal graphite cast iron with respect to a relation between any of characteristics $D_S$ showing the degree of nodularity of spheroidal graphite cast iron selected from the percentage of spheroidal graphite, the percentage of residual magnesium, the tensile strength or the elongation of the cast iron after solidification, and said $T_{EU}$, $T_{EM}$ and Z, whereby the numerical values obtained by said operational processing are displayed with a number or a pattern.

$$D_S = a + bT_{EM} + c\Delta T_E + eZ$$

where, a, b, c and e are constants and $\Delta T_E$ is a difference between $T_{EM}$ and $T_{EU}$.

BRIEF DESCRIPTION OF THE DRAWINGS

FIG. 1 is a graph showing one embodiment of a cooling curve of the hyper-eutectic SG molten iron in the process of the cooling and solidifying;

FIGS. 2I, 2II, 2III, 2IV and 2V show different graphite forms of spheroidal graphite cast iron;

FIG. 3 shows one embodiment of a method of indicating predicted result of the degree of nodularity from molten iron with a pattern;

DESCRIPTION OF THE PREFERRED EMBODIMENTS

Figure 4:
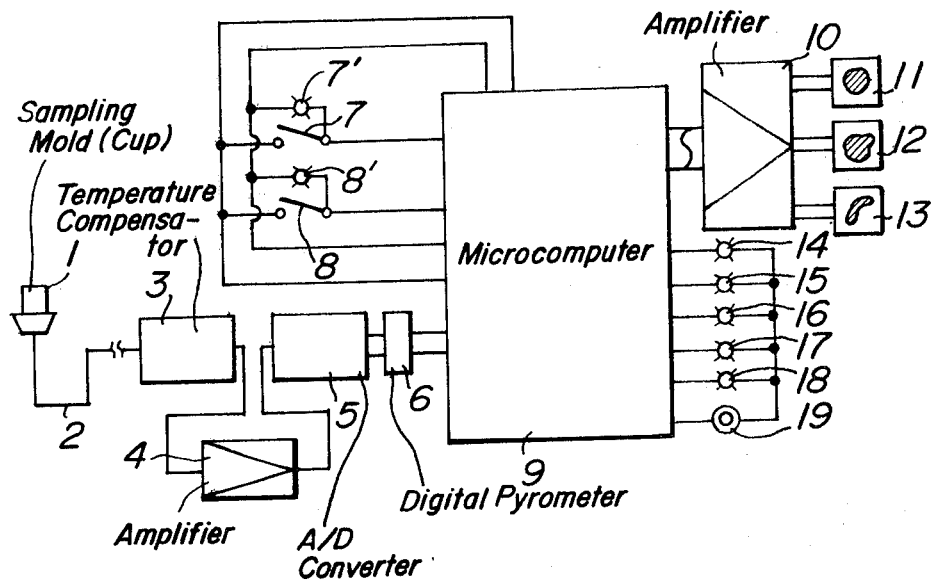
FIG. 4 is a circuit diagram showing one embodiment of an apparatus for carrying out the method according to the present invention.

The present inventors have succeeded in development of a quick and reliable method and an apparatus, wherein the process of temperature change of SG molten iron during cooling and solidification is measured by the thermal analysis and the degree of nodularity of the iron is predicted based on analysis of the result, by removing the above-mentioned disadvantages after carrying out a broad test with respect to a number of examples of SG molten iron.

At first, a so-called analog system for record-tracing a temperature change with a continuous curve, which is one of the disadvantages of the conventional thermal analysis method, is changed to a digital temperature reading system converted by an analog-digital conversion device, and thus temperatures are read out as numerical values with frequency at short time intervals to process data. The values of temperature necessary for analyzing the measured result is precisely determined by the following method, and as a result, a reading error is almost eliminated. In this case, the numerical values to be read can be a thermoelectromotive force value (mV) directly corresponding to the temperature or its function (hereinafter represented by a temperature °C.).

Further, a detecting sensitivity of temperature change (thermoelectromotive force resolution power dV) is made less than the value corresponding to 2.5° C. by amplifying the thermoelectromotive force (voltage), if necessary, so as to raise precision of measuring, and at the same time, the time interval dZ as a reverse number of frequency of temperature reading is set at a predetermined short time interval of less than 3 seconds, thereby correctly following a temperature change in the cooling process. When dV exceeds 2.5° C., a temperature necessary for analyzing the cooling process cannot be grasped sometimes, and as a result, it was confirmed from various experiments that the degree of nodularity of iron cannot be predicted. Further, at the time interval exceeding 3 seconds, a very quick temperature change in the cooling process, for example the progress from pouring a sample of molten iron into a cup to the primary crystallization cannot precisely be grasped, or a temperature necessary for analysis is overlooked, and at the same time, an error is caused for grasping a time parameter. As a result, when dZ exceeds 3 seconds, it becomes difficult to predict the degree of nodularity of molten irons.

Such kind of digital pyrometers naturally has respective predetermined values of dV and dZ from performance, but according to the object of the present invention, it is advantageous to make dV less than the value corresponding to 2.5° C. and dZ shorter than 3 seconds.

With the use of this digital pyrometer, various samples of SG molten irons having the hypo- and hypereutectic compositions were thermally analyzed by pouring into various cups having different cooling speeds. In case of rapid cooling such as within 1 minute from pouring a sample of molten iron into the cup to completion of eutectic solidification, both the compositions do not show any significant statistical correlation between various parameters grasped by thermal analysis and the degree of nodularity of molten irons. When observing microstructure of these samples, a large amount of cementite is observed due to a rapid cooling speed and its influence on the result is confirmed.

On the other hand, if the time from pouring to completion of eutectic solidification is needed more than 10 minutes, i.e. slow cooling, the cooling condition approaches the equilibrium solidification state and the result is the same as the case of low precision of dV and dZ, so that this cannot obtain a statistically significant result.

As described above, the time from pouring a sample of molten iron into a cup for thermal analysis to completion of eutectic solidification is an important factor for attaining the object of the present invention, and it is advantageous to define the time more than 1 minute and less than 10 minutes.

The time from pouring the sample into a cup for thermal analysis to completion of eutectic solidification is influenced by pouring temperature, a pouring weight, the shape of a cup and its material, cooling condition or the like, but when the cup is made of a shell mold commonly used, and in case of cooling in the atmosphere, the pouring weight is an important factor in addition to the pouring temperature. The present inventors have found from many experiments that the pouring weight of 200 g to 500 g is optimum in case of a cup with the use of a shell mold, satisfies the above condition of solidification time and obtains the best result. Therefore, the size of a cup should have inner capacity in conformity with the above pouring weight.

The cooling process read by a digital pyrometer is grasped as a continuous curve of a temperature point at each point determined by dV and dZ. Therefore, a temperature at the optional point can precisely be read as one numerical value, while a time parameter can precisely be read by integrating frequencies of a predetermined time interval determined by dZ.

One embodiment of a cooling curve of SG molten iron is shown in FIG. 1. The present inventors have tested many samples of SG molten iron having the hypo- and hyper-eutectic compositions and analyzed a relation between various parameters obtained from the numerically read cooling curve and the degree of nodularity of said molten iron by a statistical technique, i.e., a method of successively taking a parameter having the strongest correlation among parameters having significance more than a certain level and repeating a multiple regression analysis stepwise, and as a result, the parameters significant in this multiple correlation are the highest temperature $T_{EM}$ due to recalescence of eutectic solidification, the difference $\Delta T_E$ between the highest temperature $T_{EM}$ and the lowest temperature $T_{EU}$ due to undercooling of eutectic solidification and the lapse of time Z from the final time showing $T_{EU}$ and the initial time showing $T_{EM}$ by a digital pyrometer, and it was found that the multiple correlation having considerably high significance can be established. That is, the characteristic value $D_S$ showing the degree of nodularity of spheroidal graphite cast iron after solidification of molten irons, i.e., the degree of nodularity of molten irons, can be represented by the following formula (1) as a function of $T_{EM}$, $\Delta T_E$ and Z.

$$D_S = a + bT_{EM} + c\Delta T_E + eZ \ldots \qquad (1)$$

wherein a, b, c and e are constants determined by experiment.

The next important problem is how to grasp and determine temperature and time parameters which are statistically significant in practice. In the first place, in the cooling and solidification process of the SG molten iron, $T_{EU}$, i.e., a temperature value at the point from where the temperature rises, and $T_{EM}$, i.e., a temperature value at the point where the temperature rise stops, are actually grasped and determined by the following method. As to $T_{EU}$, temperature values of continuous three steps are constantly stored by a memory device, and such temperature value is employed that the temperature value of the second step is lower than those of the first and third steps by dV and continues more than 2 seconds. As to $T_{EM}$, such temperature value is employed that the temperature value of the second step is higher than those of the first and third steps by dV and continues more than 2 seconds.

The important matters herein are that the temperature difference between the second step and the first and third steps is dV and that the temperature value is employed as $T_{EU}$ or $T_{EM}$ only when the second step continues more than 2 seconds. When these conditions are not satisfied, an object of the present invention cannot be attained by grasping unnecessary or unsuitable data such as hunting of the measured temperature value or the temperature change caused by formation of an austenite ring around primary crystallized graphite observed in the SG molten iron having the hyper-eutectic composition.

$\Delta T_E$ can simply be obtained by $(T_{EM} - T_{EU})$, and Z is obtained by integrating the lapse of time dZ from the final point showing $T_{EU}$ to the initial point showing $T_{EM}$.

$T_{EM}$, $\Delta T_E$ and Z are grasped and determined by the above methods, and by substituting these numerical values, the relation of the formula (1) can just be established with statistically high significance.

In order to carry out the method according to the present invention, it is necessary to provide an apparatus comprising a sampling mold (cup) provided with a hot junction for pouring a sample of molten iron, a digital pyrometer, a memory device, a discriminator, an operation device, a display device, an integrated circuit, a control circuit and the like. That is, in the quickly predicting apparatus for the degree of nodularity of spheroidal graphite cast iron according to the present invention, as shown in FIG. 4, provision is made of a sampling mold (cup) 1 having a hot junction for pouring a sample of molten iron, the sampling mold is connected to an A/D converter 5 through a temperature compensator 3 and an amplifier 4 by means of thermocouple extension wires 2, and the output side thereof is connected to a microcomputer 9 through a digital pyrometer 6. This microcomputer 9 is composed of a memory device, a discriminator, an operation device and a control circuit, and almost all of these devices are formed by an integrated circuit. In the microcomputer 9 are provided an electric source switch 7 and its display lamp 7', a measurement start switch 8 and its display lamp 8' on the side of the input. Further, on the side of one output of the microcomputer 9 are connected a spheroidal graphite display lamp 11, a quasi-spheroidal graphite display lamp 12 and a vermicular graphite display lamp 13 through a current amplifier 10. Further, on the side of the other output of the microcomputer 9 are provided a display lamp 14 for displaying the completion of measurement, a display lamp 15 for displaying ill measurement, a display lamp 16 for displaying bad contact, an out of order of microcomputer display lamp 17, a chill alarm display lamp 18 and an alarm buzzer 19, respectively. That is, the lapse of temperature change in the cooling and solidification process of a sample of SG molten iron is grasped with frequency of a predetermined short time interval by a digital pyrometer by amplifying thermoelectromotive force, if necessary, the thus grasped lapse of temperature change is once stored by a memory device, continuously grasped temperature values of three steps and the lapse of time are discriminated by a discriminator, unnecessary temperature values are successively eliminated until the value matches with the predetermined conditions of $T_{EU}$ and $T_{EM}$ previously stored in the memory device, and the temperature values matched with the predetermined conditions are determined as $T_{EU}$ and $T_{EM}$ and stored. From these $T_{EU}$ and $T_{EM}$ is calculated a value of $\Delta T_E$ by an operation according to the previously stored operation formula of $\Delta T_E$ and stored. Further, from the final point showing $T_{EU}$ by the digital pyrometer is started to integrate the time interval dZ, the lapse of time up to the initial point showing $T_{EM}$ is determined as Z and stored in the memory device.

The values $T_{EM}$, $\Delta T_E$ and Z stored by the above method are substituted and operated by the formula (1) between $T_{EM}$, $\Delta T_E$ and Z stored as statistically significant based on a number of previous examples and the degree of nodularity of spheroidal graphite cast iron after solidification, and the obtained solution is displayed on the display device.

As described in the foregoing, the degree of nodularity of spheroidal graphite cast iron has a significant correlation with a residual Mg amount and mechanical properties, such as tensile strength, elongation and the like, other than the percentage of spheroidal graphite based on observation of the structure by a microscope. Further, according to the present inventors' experiments, even if any of them is taken as a characteristic value $D_S$ showing the degree of nodularity of molten iron, it is found that the multiple correlation having high significance can be established by only changing the constants in the formula (1) and remaining parameters $T_{EM}$, $\Delta T_E$ and Z as they are.

Accordingly, the prediction of the degree of nodularity can be displayed by any of the said degree of nodularity, i.e., the percentage of spheroidal graphite, the residual Mg amount, the tensile strength or the elongation, but one of the most preferable embodiment is to show a pattern based on the relation between classification of forms of graphite nodules (graphite forms) and amount of graphite having the classified forms.

In general, the graphite forms of spheroidal graphite cast iron are classified into 5 kinds as illustrated in FIG. 2, and the percentage of spheroidal graphite is calculated from a form coefficient corresponding to the classified form and a respective number of nodules having the classified form observed through a microscope. However, in the actual spheroidal graphite cast iron products, in almost all cases, the forms II, III, IV and V except the form I corresponding to flaky graphite, are mixed so that this system is to indicate with a pattern corresponding to the classification and the amount of these forms, and it can more visually display the degree of nodularity of spheroidal graphite cast iron in practice.

In case of displaying with a pattern, as to classification of the graphite forms, in addition to the above 4 kinds of II to V, it is possible to appropriately reduce a number of classifications of the form. That is, the actual observation through a microscope cannot clearly distinguish III from IV or IV from V, and the level of nodularity does not much differ in IV and V, so that the object can sufficiently be obtained by classifying into only 3 kinds of vermicular, quasi-spheroidal and spheroidal graphites. FIG. 3 shows one embodiment of a pattern indication. In FIG. 3, the graphite form is classified into the above 3 kinds, a section of each classification is divided into two parts and the prediction of the degree of nodularity of spheroidal graphite cast iron is divided into 7 steps. The degree of nodularity of molten iron sample is measured by a thermal analysis and analyzed according to the present invention and the result thus obtained is automatically displayed by lighting in said parts in accordance with each step. For example, when the degree of nodularity is predicted as 91%, the parts (1-1) and (1-2) are lighted.

As to the actual apparatus, poor measurement caused by bad electrical contact with a thermocouple in the cup or the like, abnormal case such as impossibility of operation caused by circuit accident in the apparatus and the like can be indicated by lighting or an alarm.

Figure 5:
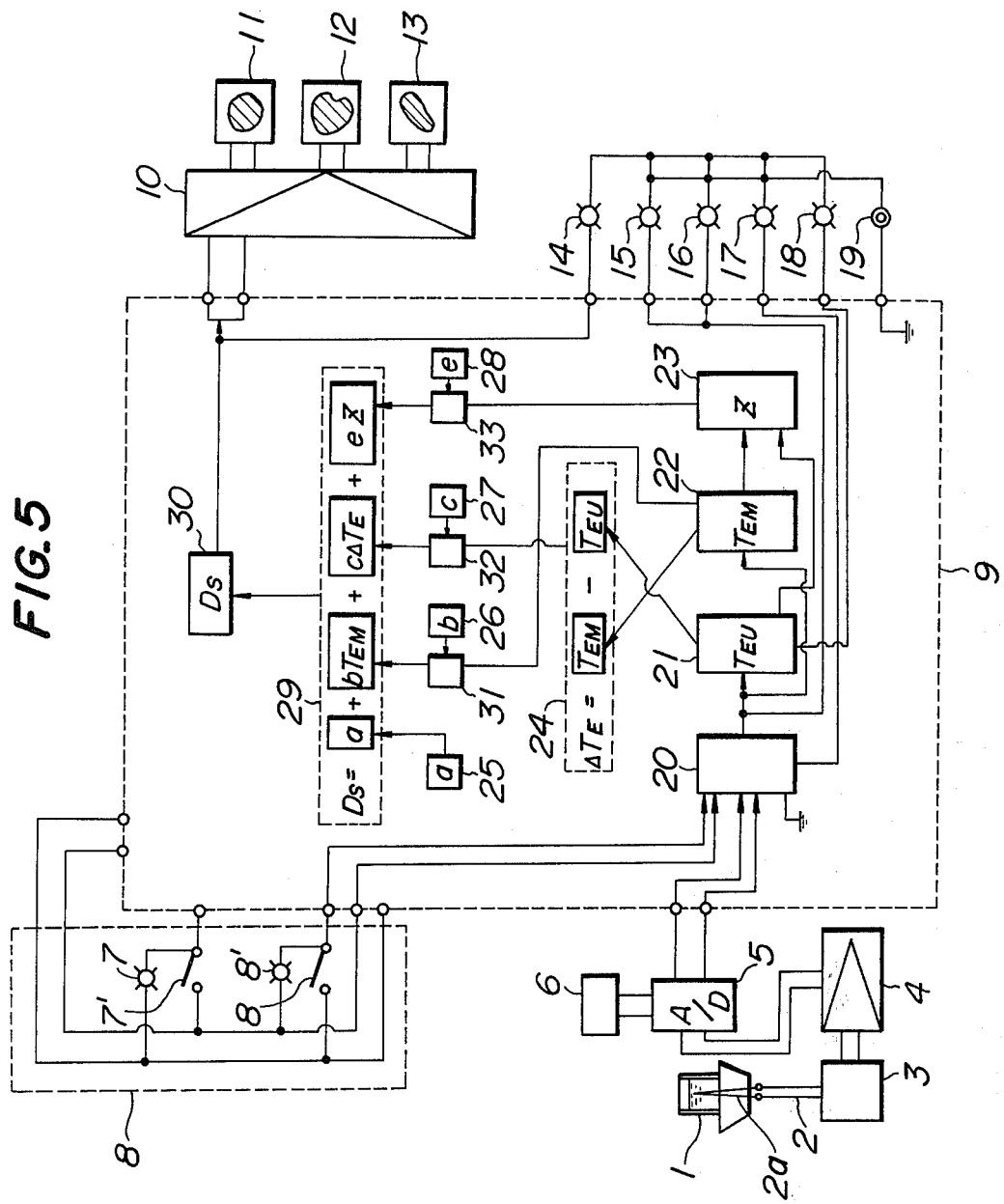
FIG. 5 is a diagram showing the circuit of FIG. 4 in greater detail.

FIG. 5 shows a circuit diagram of an apparatus according to the invention in more detail, in which reference numeral 1 is a sampling mold, and the sampling mold is provided with a thermocouple 2a for generating an electric signal by measuring the temperature of molten iron poured thereinto. A signal generated by the thermocouple 2a is transmitted to a temperature compensator 3 through a thermally compensated conductor 2 and a temperature error due to the change of ambient temperature at the cold junction of the thermocouple is compensated in said temperature compensator 3. The signal compensated by the temperature compensator 3 is amplified by an amplifier 4. An output of the amplifier 4 is supplied to an A/D converter 5 and converted from an analog signal to a digital signal therein. An output from the A/D converter 5 is supplied to a digital pyrometer 6 so as to display the temperature change continuously and is also supplied to a start circuit 20 of a microcomputer 9. The start circuit 20 is in the starting condition when an electric power supply circuit 8 is turned on; and if signals from the A/D converter 5 are supplied to a $T_{EU}$ measuring and storing circuit 21 through said start circuit 20 in the actuated condition, the $T_{EU}$ signal is discriminated by the $T_{EU}$ measuring and memory circuit 21 and the measured value $T_{EU}$ is stored therein. The output signals of the A/D converter 5 passed through the start circuit 20 are simultaneously supplied to the $T_{EM}$ measuring and memory circuit 22 and the $T_{EM}$ signal is discriminated and stored by the $T_{EM}$ measuring and memory circuit 22. The outputs of the $T_{EU}$ circuit 21 and the $T_{EM}$ circuit 22 are supplied to a Z measuring and memory circuit 23. An elapsed time Z between the time of the lowest temperature $T_{EU}$ and the time of the highest temperature $T_{EM}$ is measured by a delay time of each signal of $T_{EU}$ and $T_{EM}$ and the Z measuring and memory circuit 23 stores the thus-measured elapsed time Z. The outputs of the $T_{EU}$ measuring and memory circuit 21 and the $T_{EM}$ measuring and memory circuit 22 are supplied to a subtraction circuit 24, where the $\Delta T_E$ between $T_{EM}$ and $T_{EU}$ is calculated and the temperature difference $\Delta T_E$ between $T_{EU}$ and $T_{EM}$ is stored in said subtraction circuit 24. The output of the $T_{EM}$ measuring circuit 22 and the output of a memory circuit 26 storing a constant of b therein are supplied to a multiplication circuit 31 for obtaining a value of $bT_{EM}$ and a signal corresponding to the thus-obtained value is applied to a $D_S$ computation circuit 29. On the other hand, the output of the subtraction circuit 24 and the output of a memory circuit 27 storing a constant of c therein are supplied to a multiplication circuit 32 for obtaining a value of $c\Delta T_E$ and a signal corresponding to the thus-obtained value is applied to the $D_S$ computation circuit 29. On the other hand, the output of the Z measuring circuit 23 and the output of a memory circuit 28 storing a constant of e therein are supplied to a multiplication circuit 33 for obtaining a value of eZ, and a signal corresponding to the thus-obtained value eZ is supplied to the $D_S$ computation circuit 29. Moreover, the output of a memory circuit 25 storing a constant of a therein is directly supplied to the $D_S$ computation circuit, wherein $a+bT_{EM}+c\Delta T_E+(Z)=D_S$ is calculated.

The output of the $D_S$ computation circuit 29 is supplied to and stored in a $D_S$ memory circuit 30. The output of the $D_S$ memory circuit 30 is supplied to the amplifier 10, for lighting any one of display devices 11, 12 and 13, whereby the degree of nodularity is indicated as a pattern or figure shown in FIGS. 2 and 3 or indicated as 1 to 6 degrees by means of a digital indicator.

Reference numeral 14 shows a lamp for indicating completion of measurement and the lamp 14 displays the completion of measurement for direct observation, by lighting up when there is an output in the $D_S$ memory circuit 30. Reference numerals 15, 16 and 17 designate lamp 15 for indicating the measurement to be impossible, lamp 16 for indicating bad contact, and lamp 17 for indicating that the apparatus is in an abnormal condition. These lamps are connected to the start circuit 20 for indicating each condition whenever such abnormal conditions are detected in the start circuit 20. In addition, when measurement is impossible, or there is bad contact or an abnormal condition of apparatus or the like, an alarm display lamp 18 is lighted for indicating these abnormalities, and a buzzer 19 sounds.

The method and apparatus according to the invention will be explained with reference to examples.

EXAMPLE 1

As a result of many tests under a predetermined condition, obtained values of the constants a, b, c and e in the formula (1) are those shown in Table 1 in accordance with the use of the percentage of spheroidal graphite (%), the residual Mg amount (%), the tensile strength (kg/mm$^2$) or the elongation (%) as the characteristic value $D_S$ showing the degree of nodularity of the SG molten irons.

TABLE 1

| Degree of nodularity $D_S$ | a | b | c | e |
|---|---|---|---|---|
| Percentage of spheroidal graphite (%) | 242.367 | −5.28478 | −16.7639 | −0.161677 |
| Residual Mg amount (%) | 0.0983749 | −0.00139776 | −0.00425047 | −0.000263826 |
| Tensile strength (kg/mm$^2$) | 183.347 | −4.17676 | −3.47600 | −0.00354000 |
| Elongation (%) | 33.0796 | −0.372093 | −6.00474 | −0.0383857 |

Next, to 1 t of the base iron having the chemical composition of C 3.56%, Si 1.62%, Mn 0.52%, P 0.031% and S 0.019% (hypo-eutectic composition) before the nodulizing treatment was added 0.8% of an Fe-Si-Mg alloy containing 8% of Mg by a sandwich system, the thus treated SG molten iron was poured into a cup which require 3 minutes from the pouring of a sample of molten iron to the completion of eutectic solidification and a so-called Y-block mold, immediately after the nodulizing treatment and 15 minutes after the treatment, measured by the method and the apparatus according to the present invention, calculated the degree of nodularity by applying said formula, and the prediction results (the percentage of nodularity of spheroidal graphite %, the tensile strength kg/mm$^2$, the elongation %, the residual Mg amount %) are compared with those actually measured with the use of the Y block sample. The result is shown in Table 2.

TABLE 2

| | | Percentage of spheroidal graphite (%) | Tensile strength (kg/mm$^2$) | Elongation (%) | Residual Mg amount (%) |
|---|---|---|---|---|---|
| Immediately | Prediction by method and apparatus according | 85.6 | 56.3 | 12.2 | 0.042 |

TABLE 2-continued

| | | Percentage of spheroidal graphite (%) | Tensile strength (kg/mm²) | Elongation (%) | Residual Mg amount (%) |
|---|---|---|---|---|---|
| after nodulizing treatment | to the invention Measurement result of Y block sample | 86.8 | 57.9 | 13.4 | 0.039 |
| 15 minutes after the treatment | Prediction by method and apparatus according to the invention | 65.1 | 55.0 | 8.0 | 0.025 |
| | Measurement result of Y block sample | 67.0 | 53.4 | 8.6 | 0.028 |

EXAMPLE 2

To 1 t of the base iron having the chemical composition of C 3.82%, Si 1.93%, Mn 0.38%, P 0.029% and S 0.017% (hyper-eutectic composition) before the nodulizing treatment was added 0.8% of an Fe-Si-Mg alloy containing 8% of Mg by a sandwich system, the thus treated SG molten iron was poured into a cup which require 4 minutes from the pouring of a sample of molten iron to the completion of eutectic solidification, and a Y block mold, immediately after the nodulizing treatment and 15 minutes after the treatment, measured by the method and the apparatus according to the present invention, calculated the degree of nodularity by applying the formula described in Example 1, and the prediction results (the percentage of nodularity of spheroidal graphite %, the tensile strength kg/mm², the elongation %, the residual Mg amount %) were compared with those actually measured with the use of the Y block sample. The result thereof is shown in Table 3.

TABLE 3

| | | Percentage of spheroidal graphite (%) | Tensile strength (kg/mm²) | Elongation (%) | Residual Mg amount (%) |
|---|---|---|---|---|---|
| Immediately after nodulizing treatment | Prediction by method and apparatus according to the invention | 92.0 | 46.7 | 21.6 | 0.048 |
| | Measurement result of Y block sample | 88.4 | 45.1 | 22.8 | 0.052 |
| 15 minutes after the treatment | Prediction by method and apparatus according to the invention | 66.5 | 43.1 | 16.2 | 0.029 |
| | Measurement result of Y block sample | 73.2 | 45.6 | 14.4 | 0.027 |

As apparent from the above examples, it is clear that the quick prediction of the degree of nodularity of spheroidal graphite cast iron from molten iron samples by the method and the apparatus according to the present invention has reliability sufficient enough to spheroidal graphite cast iron having both the hypo- and hyper-eutectic compositions.

What is claimed is:

1. A method of producing spheroidal graphite cast iron of a high degree of nodularity, comprising:

subjecting a quantity of molten iron containing carbon to a nodulizing treatment;

pouring a sample of said quantity of molten iron into a sampling mold having a thermocouple for measuring a temperature change of molten iron poured into the mold and converting the value into electrical signal;

cooling said sample of molten iron with the cooling conditions adjusted such that the time duration after the pouring of the sample of molten iron into the sampling mold up to the completion of the eutectic solidification is within a range of 1 to 10 minutes;

measuring the lowest temperature $T_{EU}$ due to undercooling and the highest temperature $T_{EM}$ due to recalescence subsequent to the undercooling and the time elapsed (Z) between the occurrence of the lowest temperature $T_{EU}$ and the occurrence of the highest tmperature $T_{EM}$ by said thermocouple during the cooling period;

sampling the analogue signals derived from said thermocouple at predetermined short time intervals of less than 3 seconds in sampling means;

converting the sampled analogue signal into a digital signal in an analogue-digital converter;

successively determining and storing in a computer the values for the lowest temperature $T_{EU}$ due to undercooling and for the highest temperature $T_{EM}$ due to recalescence subsequent to the undercooling;

determining and storing in the computer the elapsed time Z from the occurrence of the lowest temperature $T_{EU}$ and the occurrence of the highest temperature $T_{EM}$;

storing in the computer predetermined constants (a, b, c, e);

processing the value of the degree to be determined of nodularity from the temperature $T_{EM}$, $T_{EU}$, the constants (a, b, c, e) and the measured time (Z) according to a predetermined function ($a+b \cdot T_{EM}+c\Delta T_E+eZ$) in an operational processing circuit of the computer;

displaying the achieved value of the degree of nodularity with a digital or analogue display; and casting the rest of said quantity of molten iron if the displayed value of the degree of nodularity is at least 61%.

2. A method as claimed in claim 1, in which the rest of said quantity of molten iron is cast without further nodulizing treatment.

3. A method as claimed in claim 1, in which the displayed value of the degree of nodularity is at least 71%.

4. A method as claimed in claim 1, in which the displayed value of the degree of nodularity is at least 81%.

5. A method as claimed in claim 1, in which the displayed value of the degree of nodularity is at least 91%.

* * * * *